(12) United States Patent
Schilling et al.

(10) Patent No.: US 6,937,787 B2
(45) Date of Patent: Aug. 30, 2005

(54) OPTICAL HIGH SPEED ROTARY JOINT

(76) Inventors: Harry Schilling, Klostergarten 15a, 85072 Eichstätt (DE); Georg Lohr, Allingerstrasse 75, 82223 Eichenau (DE)

( * ) Notice: Subject to any disclaimer, the term of this patent is extended or adjusted under 35 U.S.C. 154(b) by 135 days.

(21) Appl. No.: 10/358,986

(22) Filed: Feb. 5, 2003

(65) Prior Publication Data

US 2004/0141686 A1 Jul. 22, 2004

(30) Foreign Application Priority Data

Jan. 21, 2003 (DE) .......................................... 103 02 435

(51) Int. Cl.[7] .............................................. G02B 6/26
(52) U.S. Cl. .......................................... 385/26; 385/39
(58) Field of Search ............................ 385/26, 15–52, 385/39; 307/10.1

(56) References Cited

U.S. PATENT DOCUMENTS 6,759,759 B2 * 7/2004 Kojima et al. ............. 307/10.1

* cited by examiner

*Primary Examiner*—Frank G. Font
*Assistant Examiner*—Michael P. Mooney
(74) *Attorney, Agent, or Firm*—Kevin L. Daffer; Daffer McDaniel, LLP

(57) ABSTRACT

What is described here is a device for the transmission of modulated optical signals between two units supported for rotation relative to each other, by means of optical transmitters and receivers. The total of optical transmitters and receivers is three at minimum. A switching unit selects optical transmitters or receivers, respectively, for transmission in dependence on the position as well as in a synchronised manner so that the optical path will always have the same orientation as the direction of movement. Moreover, means are provided for suppressing multiply transmitted data.

8 Claims, 4 Drawing Sheets

OPTICAL HIGH SPEED ROTARY JOINT

BACKGROUND OF THE INVENTION

1. Field of the Invention

The present invention relates to a device for broad-band transmission of optical signals between units rotatable relative to each other. Such devices are preferably employed in computer tomographs.

2. Prior Art

Various devices have become known for the transmission of optical signals between units rotatable relative to each other, particularly with a free inner diameter. For their application in a computer tomograph, such devices must present large free inner diameters in the order of 1 meter. The peripheral speed in rotation may range in the order of 20 m/s. At the same time, data rates of more than 1 gigabit per second (GBaud) should be possible.

The U.S. Pat. No. 4,109,997, for example, discloses an optical rotary transformer wherein the light is convoyed along the periphery by reflection on two opposite surfaces. For coupling or decoupling the light, optical conductors or glass fibres are provided, with the light beam being focused by means of lenses. This device, however, presents quite a number of disadvantages. For instance, the bandwidth is strongly restricted. A wideband data transmission with period lengths of the modulation signal, which are substantially shorter than the delay of the signal along the periphery of the device, is not possible in this case because when the receiver is positioned in the vicinity of the transmitter, multiple-way reception of signals occurs. In this manner, signals are received simultaneously over a short way from the receiver and, at the same time, signals are received that have been reflected at least once along the periphery of the device. The delay difference must be small, compared against the period length of the modulation signal. Hence, with an inner diameter of roughly one meter, a total delay along the periphery of roughly 10 nanoseconds is achieved. As a consequence, in the transmission of digital signals, it is possible to realize bit periods of 50 nanoseconds at maximum, which corresponds to a maximum transmission rate of 20 MBaud.

For a reduction of the attenuation along the transmission distance and for enlargement of the bandwidth that can be transmitted, U.S. Pat. No. 5,354,993 and U.S. Pat. No. 6,104,849, propose a transmission in several shortened segments. U.S. Pat. 5,354,993 describes a transmission in the free space while U.S. Pat. No. 6,104,849 discloses a mirrored trough. The shortened segments create a reduced attenuation. In this case, the maximum bandwidth is inversely proportional to the length of the segments. In this manner, it is possible to achieve a wider bandwidth with shorter segments. As a matter of fact, however, this requires also a correspondingly higher number of optical transmitters or receivers, respectively, in order to cover the complete periphery of the circle. As a result, the system costs are increased in proportion to the bandwidth.

The present invention is based on the problem of configuring a comparatively low-cost device for the transmission of optical signals between two units rotatable relative to each other, in such a way that a reliable transmission will become possible with high data rates. In this approach, it should also be possible to transmit data, in particular, whose length of propagation of an individual bit is small, compared against the distance of individual optical transmitters or receivers. Here, the length of propagation of an individual bit is defined by the product of the bit length and the propagating speed in the medium, which is in the order or the velocity of light.

One inventive solution to this problem is defined in the independent Patent Claims. Improvements of the invention are the subject matters of the dependent Patent Claims.

The invention is based on the idea of transmitting optical signals in the direction of movement, particularly for the transmission in transmission systems synchronised in terms of clock cycle. Suitable transmitters or receivers, respectively, are always selected as a function of the position in such a manner that an appropriate signal transmission quality will be ensured along the direction of movement. Moreover, means are provided to eliminate data transmitted in multiple numbers.

Due to the Doppler effect, a positive frequency shift is achieved so that, due to the movement, the receiver will receive a data rate that is higher than the data rate emitted by the transmitter. This frequency shift is so slight that it can be processed, without any problems, by the usually employed synchronous receivers. When, for instance, in a typical computer tomograph with a data rate of 5 GBit per second and with a movement of the two units relative to each other of two revolutions per second, the mechanical movement deriving from the known formula of the Doppler effect for a typical periphery of the mobile units of 5 meters and for a resulting peripheral speed of 10 m/s creates a frequency shift by 3.34e to 8 Hz, in correspondence with a frequency modification by 166 Hz. Accordingly, 2.5e9 bits+83 bits are transmitted within one revolution, i.e. within 0.5 seconds. These additionally transmitted bits are now eliminated from the data flow by suitable means.

In order to ensure that data will be transmitted exclusively in the direction of movement and that, at the same time, an unambiguous data reception will be possible a change-over between at least two transmitters or at least two receivers, respectively, is required. The term of "transmission along the direction of movement" must be considered here in an integral form. What is essential for the proper functioning of the invention is the aspect that from one change-over time to the next change-over time from a first transmitter to a second transmitter or from a first receiver to a second receiver, respectively, the integral of the frequency shifts is positive. This can be achieved by the provision that individual transmitters pass by individual receivers in a succession corresponding to the direction of propagation of the optical signals. In the intervals therebetween, the question of whether the movement comes to a halt or whether even a movement in the opposite direction takes place, does not take any influence on the function. In the case of a movement in the opposite direction, however, an active optical transmitter must not pass by an active optical receiver, as a matter of fact, because else a negative frequency shift would result in data losses.

In the above-quoted U.S. Pat. No. 6,104,849, for instance, several optical transmitters are alternating in engagement with a receiver. As a matter of fact, however, these transmitters are permanently activated. Reception of the signals by the receiver is possible whenever an optical receiver is engaged with the optical conductor. To ensure a continuous transmission engagement with a second optical transmitter is necessary at least at those sites where an optical transmitter is passing along the optical receiver, which second transmitter then performs the transmission function. As a result, the signals from two optical transmitters are superimposed, at least for a short period. As these signals cannot be discriminated by the optical receiver the latter adds the signals. Hence, an unambiguous signal transmission is possible only when the bit length of a signal is substantially shorter than the delay difference between the two signals.

In an expedient improvement of the invention, this restriction is eliminated by the change-over between the optical transmitters. The change-over can be controlled, for instance, as a function of time or in dependence on the position.

The propagation of the optical signals from the optical transmitter to the optical receiver progresses in the same direction as the rotational movement of the first unit relative to the second unit. When only one first optical transmitter activated by the switching unit approaches the optical receiver, signals can be transmitted up to that point of time by which the optical transmitter passes by the optical receiver. By that point or time at the latest, now the switching unit most deactivate the first optical transmitter and activate a second optical transmitter that has been moved by the rotational movement into the receiving range of the optical receiver. As the optical signals from the second transmitter must now cover a longer distance than the signals of the first transmitter, they arrive there too late. Hence a gap is created in signal transmission. The receivers usually employed for serial data flows synchronize their internal clock by means of a PLL element (phase locked loop) in relation to the bits of the received data flows. When this data flow is now interrupted, the PLL element becomes non-synchronized and requires new synchronization. The data received during the synchronization phase is usually not suitable for exploitation because it is scanned partly by the wrong points of time during the transient phase of tho PLL element and is hence not correctly reproduced. For this reason, an interruption of the data flow should be avoided. This can be achieved, for instance, by activating the second optical transmitter as early as prior to the deactivation of the first transmitter. The difference in time corresponds preferably to the delay period of the optical path towards the final optical transmitter. This provision hence ensures that the signals of the second optical transmitter reach the receiver directly after the first optical transmitter has been stopped. In order to avoid a repeated synchronization of the PLL element, the interval between the first and the second optical transmitters is so selected that is corresponds to a multiple of tho optical path of a bit in the data flow. With this configuration, now a certain number of bits is transmitted a second time in proportion to the distance between the first optical transmitter and the second optical transmitter. Hence, in the case of air with a propagation rate c in correspondence with the velocity of light c=c0 as optical medium, for instance, the propagation length of a bit corresponds hence to roughly 5 cm at a data rate of 5 gigabits per second. As a result, the distance between the first and second optical transmitters is preferably selected to be multiples of 6 cm, 12 cm, 18 cm, 24 cm, etc.

In order to avoid interference in the receiver, a controller is provided in the second unit, which suppresses the transfer of the bits received twice or signals the multiple reception of bits in a subsequent analyser unit so that these bits can be can be cancelled or ignored, respectively. Hence, the signals are still available for PLL synchronisation in the receiver but then they are not further processed.

For a particularly expedient configuration of the elimination of the information transmitted in excess, the distance between a first optical transmitter and a second optical transmitter is so designed that it corresponds to a multiple of the propagation length of a data package. Various receiver components have become known that combine, for example, 8, 10, 12 or even 20 bits in a single data package that is also referred to as data word or frame. The propagation length of a data package is hence proportional to the length of the word. On the basis of the data rate from the previous example, propagation lengths of 48 cm, 60 cm, 72 cm or even 120 cm are achieved. When the distance between individual transmitters is dimensioned as a multiple of the propagation length of a data package it is not necessary to eliminate individual bits but rather complete data packages by means of the controller. The removal of individual data packages may be triggered, for instance, by a control signal emitted by the switching unit between the transmitters by the time of change-over.

It is not necessary that all the transmitters or receivers be arranged at equal distances from each other. This should be illustrated by a dimensioning example. When in the present example a data package size of 10 bits is used for transmission in the manner deriving, for instance, with the widely used 8B/10B coding, the scope of transmission is selected for a distance of 540 cm (=90*6 cm) in correspondence with the propagation length of 90 bits. For example, now four transmitters can be installed at a respective spacing of 120 cm—in correspondence with 20 bits and hence two data packages—as well as a transmitter at a distance of 60 cm—in correspondence with 10 bits and one data package. By the time of change-over then the corresponding number of data packages must be eliminated. For this example the assumption was applied that all the optical transmitters are connected to the data transmitter (7) by the same lengths of line. Different lengths of line, however, are conceivable, too. When it is not possible, for instance, to mount an optical transmitter at the envisaged position the transmitter may be offset, for example along the direction of movement, whilst a feeder line to the data transmitter is provided which is extended in correspondence with the reduction in the length of the optical path.

A particularly expedient embodiment is obtained when the controllers, which are present in the majority of data receivers, are incorporated into the operation by an inventive array. For example, the majority of the known data receivers comprise means for checking the frames of the data packages and often also for checking the coding for consistency. When a frame or coding error is detected this error is signalled to the outside and the respective data package is selectively discarded by the data receiver or by a joining unit, respectively. Often other types of packages are used as well, which are transmitted, for instance, in a state of rest. Such packages are not transferred either. Therefore, the contents of the multiply transmitted data packages is so modified—for signalling multiply transmitted data packages—that a data receiver will recognise them as defective or as signalling a state of rest.

Such a modification is possible, for instance, by optical means with optical super-position of the signals, which furnishes a troubled received signal, or also by electrical means with influence on the input signals of an optical transmitter. Some or all data of a package could be inverted, for example.

In another expedient embodiment of the invention, the first unit comprises one or several optical transmitters that are activated by a switching unit in dependence on the position. Two optical receivers are provided on the second unit for receiving the optical signals. The optical signals propagate in the same direction as the direction of the rotational movement of the first unit relative to the second unit. The optical transmitters are activated, preferably permanently, at least in the vicinity of the optical receivers. To permit an unambiguous reception of the signals the optical receivers are sequentially activated by a switching unit.

The sequence of operation is as follows:

Initially, a respective first transmitter as well as a first optical receiver are activated and in optical connection. Seen in the direction of propagation of the optical signals and also in the direction of movement from the first unit to the second unit, a second, non activated optical receiver is disposed ahead of the activated optical receiver. On principle, by this point of time reception by the second, non activated optical receiver would also be possible. When now, on account of the movement, the first optical transmitter passes by the second optical receiver reception is still possible only by the activated first optical receiver. Reception by the second (not activated) optical receiver would no longer be possible as the latter is already located behind the first transmitter. Then the switching unit performs a change-over from the first optical receiver to the second optical receiver. The point of time of change-over can be optionally selected as long as the first transmitter is located between the second receiver and the first receiver. After this change-over, now the second optical receiver receives light from a further, second optical transmitter that has moved into the receiving range of the second optical receiver. The second optical receiver now receives the delayed data from the second optical receiver. Here, too, the controller serves to cancel the multiply transmitted data. At any subsequent point of time whatsoever within a time window, after the passage of the first optical transmitter by the first optical receiver, and as long as the second optical receiver is still in engagement with the second optical receiver, the switching unit now changes over from the second optical receiver to the first optical receiver. In order to avoid phase jumps, the optical receivers are preferably disposed so close to each other that the distance between the two receivers is substantially smaller than the length of propagation of one bit. With reference to the previously discussed example, at a length of propagation of one bit of 6 cm, a distance of 2 cm between the two receivers can be well realised. According to an alternative, the distance between the two receivers can also be selected to correspond to a multiple of a length of propagation of one bit or of one data package. In such a case, the controller must also cancel multiply transmitted bits or data packages, respectively.

Particularly in computer tomographs, only one direction of movement is provided in operation. For this reason, the definition of the direction of movement, which must correspond to the direction of the optical propagation, does not involve any restriction in terms of functionality. In a few cases, however, it may be desirable to permit also a movement in the opposite direction. Such an opposite movement is possible with an inventive embodiment in correspondence with Claim 1 even in small angular zones as long as an active transmitter does not pass along an active receiver. When a revolution over a wider angular zone is desired the transmitter must be operated with a data rate that is at least increased by the Doppler effect and the emission of a corresponding number of bits must be repeated directly after the change-over as the latter number of bits is lost due to the change-over operation. A detailed discussion of this process is dispensed with here because it is performed in reverse order, compared against the previously described change-over operation. Such a device is independently applicable or may also be employed in combination with an appropriate device according to Claim 1.

The statements presented in this document relate to an optical transmission path between optical transmitters and optical receivers, which are connected to each other by means of a general optical medium. An optical conductor, an optical waveguide or even a gas such as air, for instance, as well as a liquid may be such an optical medium.

Another expedient embodiment of the invention avoids the necessary adaptation of the geometry to the data rate. To this end, controllable time-lag devices such as delay lines are incorporated into the feeder line. It is possible to compensate the difference in the lengths of the trajectories in correspondence with the movement by a controller by means of the incorporation of an additional delay provision. A compensation can also be performed for adaptation to individual bits or also to data packages. When, for example, an adaptation of the periphery to 540 cm is not possible—like in the example described above—an adaptation to 510 cm in correspondence with 85 bits is also sufficient. In such a case, half a data package, corresponding to five bits, is left over during one revolution. Now an additional delay corresponding to five bits can be set during a second revolution. At the end of the revolution, five further bits have accumulated so that a complete data package—corresponding to 10 bits—can be eliminated from the data flow. Hence, the subsequent revolution can commence again with a transmission cycle without a delay.

An inventive method of wideband transmission of data between two units rotatable relative to each other comprises the steps of providing serial electrical data, of converting them into optical data, of transmitting the data between optical transmitters and receives along the direction of movement, of changing over between different transmitters and receivers in such a manner that the direction of transmission along the direction of movement is retained, as well as the step of eliminating multiply transmitted data.

BRIEF DESCRIPTION OF THE DRAWINGS

The invention will be described in the following by exemplary embodiments, without a limitation of the general inventive idea, with reference to the drawings.

DETAILED DESCRIPTION OF THE INVENTION

Figure 1:
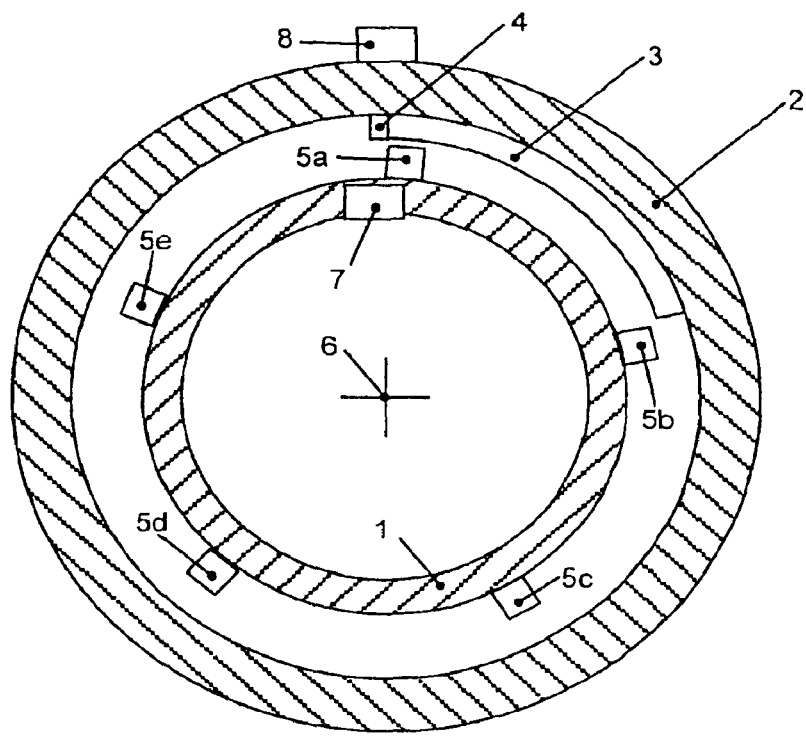
FIG. 1 is a general schematic view of an exemplary embodiment of an inventive device.

FIG. 1 is a schematic sectional view of an exemplary embodiment of an inventive device. This figure shows the first unit (1), which is supported for rotation relative to the second unit (2) about the axis of rotation (6). A data transmitter (7) serves to generate a serial data flow. This data transmitter is connected via lines—that are not shown here for reasons of clarity of the illustration—to the individual optical transmitters (5a, 5b, 5c, 5d, 5e). In this manner, the data transmitter can be configured for emitting electrical signals. In such a case, the optical transmitters are configured, for instance, in the form of laser diodes or LEDs. The data transmitter may, however, equally be configured for the emission of optical signals so that the optical transmitters, whose transmitting function is related only to the optical transmission path, are preferably designed as passive optical coupler elements.

Figure 2A:
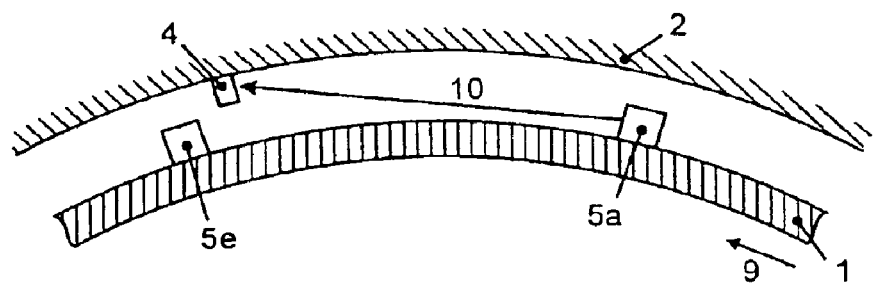
FIGS. 2a to 2c are schematic illustrations of the flow of steps for change-over between successive transmitters.
Figure 2B:
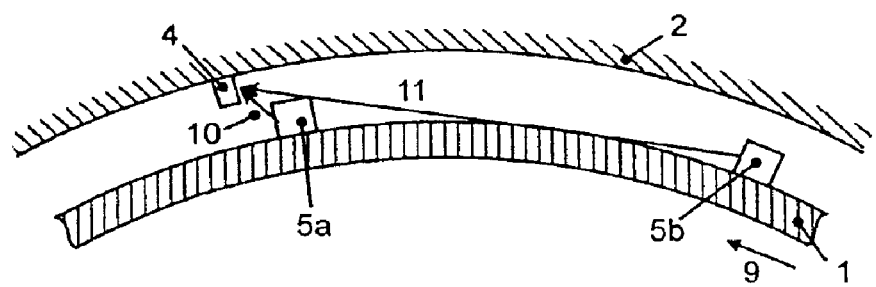
Figure 2C:
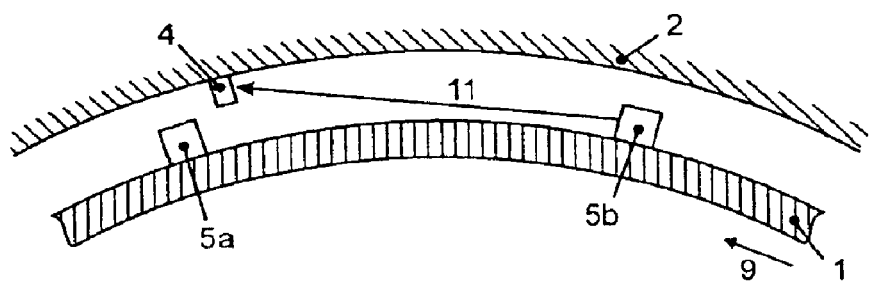

FIGS. 2a to 2c are schematic illustrations of the flow of steps for change-over between two transmitters disposed in succession. The direction of movement between the first unit (1) and the second unit (2) is indicated by the directional indicator (9). As can be seen in FIG. 2a, initially a connection is established by the first light beam (10) between an optical transmitter (5a) and the optical receiver (4). With a continuing approach to the optical receiver, the length of the path of the first light beam (10) is shortened, as is illustrated in FIG. 2b. Now a second optical transmitter (5b) has arrived, too, within the receiving range of the optical receiver. Now a change-over from the first optical transmitter to the second optical transmitter is performed, preferably in a manner synchronised in terms of clock cycle or in terms of packages, respectively, so that the connection is now established exclusively by the second light beam (11). In accordance with FIG. 2c, the first optical transmitter has moved behind the receiver in a continuing movement. In this position, this transmitter can no longer operate in transmission because it moves now away from the receiver. Transmission is now rather performed between the second optical transmitter and the optical receiver via the second light beam.

Figure 3:
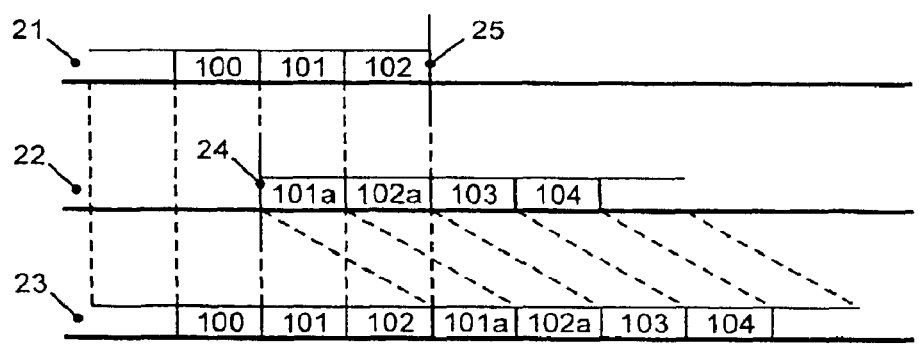
FIG. 3 illustrates a schematic view of the chronological flow of the steps for change-over between successive transmitters.

FIG. 3 is a schematic illustration of the flow of the steps for change-over between successive transmitters. The first time-based diagram (21) illustrates the chronological flow of individual data packages (100, 101, 102) as they are emitted by the first optical transmitter (5a). The data packages (101, 102, 103, 104) of the second optical transmitter (5b) are shown in the second time-based diagram (22). The third time-based diagram (23) finally shows the sequence of the data packages received by the receiver (4). The combined data packages constitute the data flow to be transmitted, in the sequence of the numbering. In the beginning of the sequence—in correspondence with the first time-based diagram—the data packages are emitted by the first optical transmitter. By the first point of time of change-over (24), the second optical transmitter is started. As the optical path of the second light beam is longer than the path of the first light beam—cf. FIG. 2b—the data packages (101a, 102a, 103, 104) of the second transmitter arrive later in the receiver. The difference between the optical trajectories, i.e. the difference between the lengths of the second light beam and the first light beam, should be so dimensioned that it corresponds to an integer number of bits or data packages. When the data packages from the second transmitter arrive at the receiver the first transmitter may be switched off by a second point of time for change-over (25). The receiver receives correspondingly the data packages 101 and 102 in duplicate in this example. These data packages must now be cancelled by the means provided to this end. When, for example, the data packages 101 or 102, respectively, are selectively interfered with, optionally by the first or second transmitter, the receiver can recognise them automatically as invalid and eliminate them from the data flow. Such interference by optical superposition of the signals occurs when the first transmitter is switched off only with a delay by two data packages. When the data packages are selectively interfered with a synchronous change-over between the two transmitters is not required because, on account of the mechanical dimensioning wherein the difference in delays corresponds to a multiple of the length of propagation, synchronisation in terms of clock cycle is present anyhow.

Due to an optional change-over within the data packages, an additional distortion of the contents arises.

As an alternative of the duplicate emission of data packages, which are described here, it is also possible to select the switching times in such a way that duplicate transmission does not take place, which means that simultaneously with switch-off of the first transmitter the second transmitter is switched on. As a matter of fact, however, a pause without transmitted signal occurs in this case. Such a pause involves, however, high demands on the PLL elements employed in the data receivers so that the latter will not be de-synchronised.

FIGS. 4a to 4d show a further embodiment of the invention with two optical receivers (4a, 4b) and several optical transmitters (5a, 5b), wherein, by contrast to the previous embodiment, the change-over is performed on the receiver side. In that embodiment, it is expedient to use an optical medium or an optical conductor with a comparatively high attenuation, which, in its turn, is mostly less expensive to produce than a low-attenuation medium.

Figure 4A:
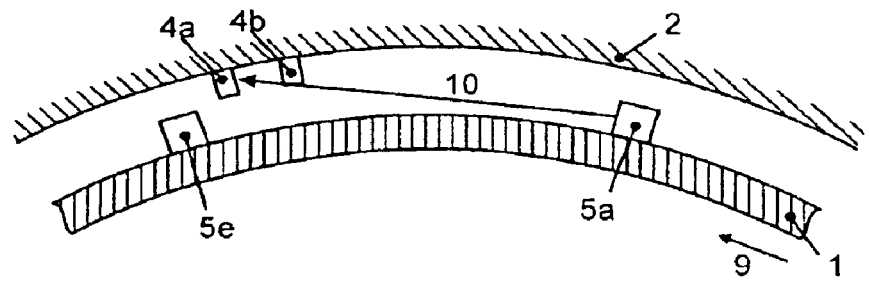
FIGS. 4a to 4c show a further embodiment of the invention.
Figure 4B:
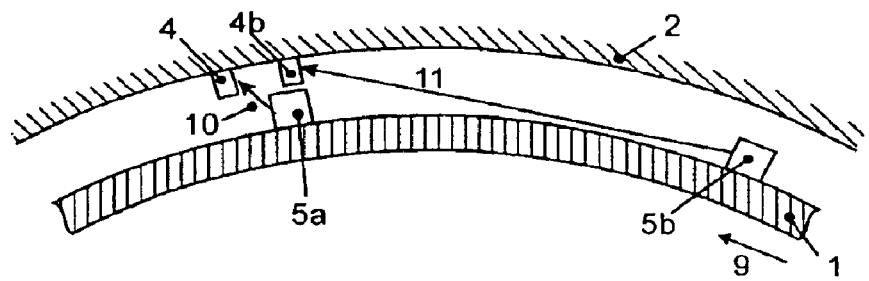
Figure 4C:
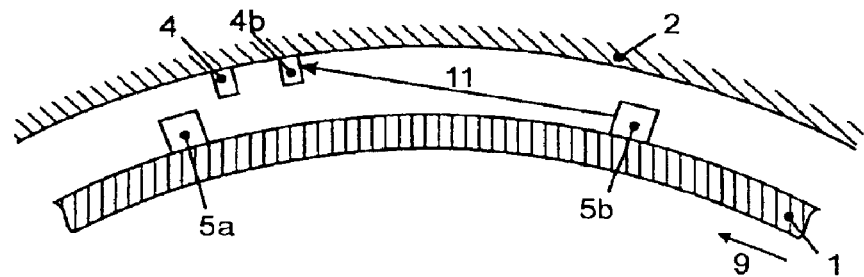
Figure 4D:
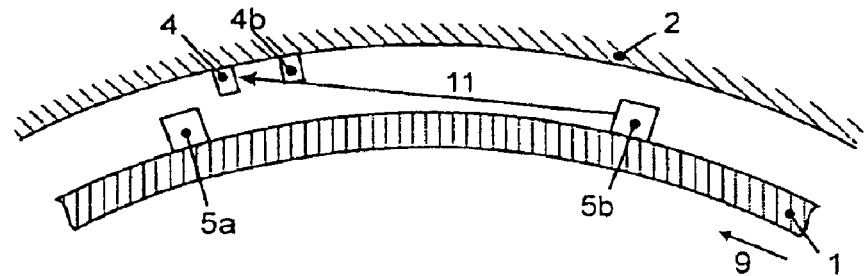

According to FIG. 4a, initially a first optical transmitter (5a) and a first optical receiver (4a) communicate with each other. As the first optical transmitter continues its approach to the optical receivers a second optical transmitter (5b) comes within the receiving range of the first optical receiver. On account of the attenuation by the optical medium used for transmission, the signal (10) of the first optical transmitter is substantially stronger than the signal (11) of the second optical transmitter so that this signal of the second optical transmitter does not yet take an influence on the transmission. It is now possible at any point of time whatsoever that a changeover of reception from the first optical receiver to the second optical receiver takes place whilst the first optical transmitter is located between the first optical receiver and the second optical receiver. The second optical receiver now receives exclusively the signal (11) from the second optical transmitter, as is illustrated in FIG. 4c. Reception of the signal (10) from the first optical transmitter is no longer possible as the latter is already behind the second optical receiver. The changeover from the second optical receiver to the first optical receiver takes place at an optional subsequent point of time after the passage of the first optical transmitter by the first optical receiver, as is illustrated in FIG. 4d, so that now the latter receives the signal from the second optical receiver and transfers it to the data receiver. For a particularly simple design of this changeover operation the distances between the first optical receiver and the second optical receiver become preferably smaller than the optical length of path of a bit.

Figure 5:
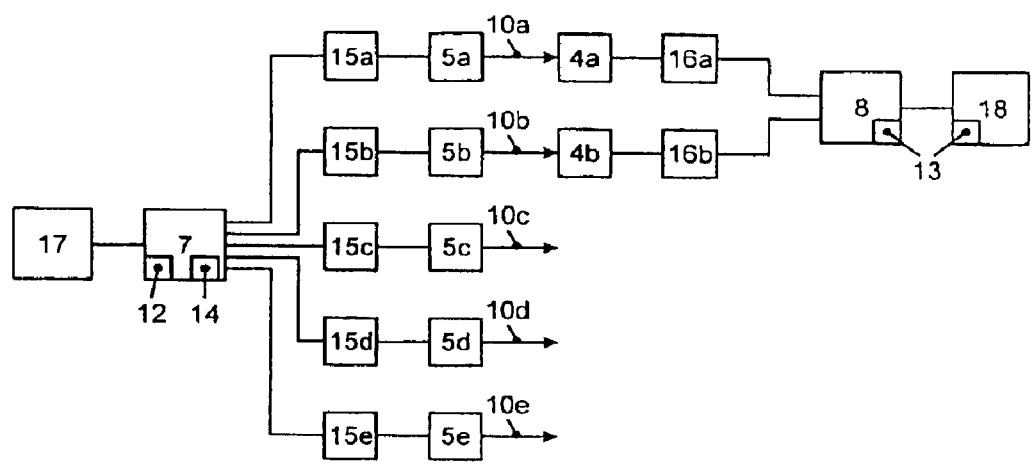
FIG. 5 is a block diagram illustrating an inventive device.

FIG. 5 is a block diagram of an inventive device. A data sink (17) supplies a data transmitter (7) with data that generates at least one serial data flow as output signal for controlling at least one optical transmitter (5a, 5b, 5c, 5d, 5e). An optional switching unit (12), which activates or deactivates the individual optical transmitters, is connected to the data transmitter. Moreover, this switching unit signals to the data transmitter, if necessary, that data packages are to be generated that which the data receiver can recognise as faulty. Optionally, an additional means (14) is provided for repeating the transmission of data. Optional time-lag devices (15a, 15b, 15c, 15d, 15e) are disposed between the data transmitter and the optical transmitters, which may, of course, also be integrated into the data transmitter or into optical transmitters, respectively. The output signals (10a, 10b, 10c, 10d, 10e) of the optical transmitters are optionally transmitted to at least one optical receiver (4a, 4b) in dependence on the position. The signals of the optical receivers are communicated to a data receiver for analysis. Optional time-lag devices (16a, 16b) are disposed between optical receivers and the data receiver. These devices, too, may optionally be integrated into the data receiver or into optical receivers, respectively. The data receiver supplies the decoded data flow to the data sink. Furthermore, at least one means is provided for cancellation of multiply transmitted data optionally in the data receiver or in the data sink, respectively. Such an inventive device is, of course, suitable for application not only for the transmission between units rotatable relative to each other but also inn any other units and also on other paths of movement.

List of Reference Numerals 1 first unit
2 second unit
3 optical conductor
4 optical receivers (4a, 4b)
5 optical transmitters (5a, 5b, 5c, 5d, 5e)
6 axis of rotation
7 data transmitter
8 data receiver
9 directional indicator
10 first light beam
11 second light beam
12 switching unit
13 means for cancellation of multiply transmitted data
14 means for repeating the transmission of data
15 time-lag device ahead of optical transmitters
16 time-lag device behind optical receivers
17 data source
18 data sink
20 data flow from the first optical transmitter
21 data flow from the second optical transmitter
22 data flow at the optical receiver
23 first switching time
24 second switching time
100–104 data packages

What is claimed is:

1. Device for the transmitting of optical signals between a first device and a second device, both devices being rotatable relative to each other, comprising:
at least one optical transmitter attached to said first device for emission of optical signals;
at least one optical receiver attached to said second device for receiving said optical signals;
at least one optical medium, preferably a light guide for transferring or guiding said optical signals;
wherein said optical transmitters or receivers are arranged so that at any time at least one of said optical transmitters is connected via one of said optical media to at least one of said optical receivers; and
wherein the total of the numbers of optical transmitters and optical receivers amounts to at least three and that the sense of rotation between said first device and said second device is equal to the sense of the direction of propagation of said optical signals, and that at least one switching unit is provided that selects optionally one of a plurality of optical transmitters or one of a plurality of optical receivers in such a way that precisely one optical transmitter and one optical receiver is activated at one time for transmission between said first device and said second device and that means are provided in said second unit for deleting of multiply transmitted data.

2. Device according to claim 1, wherein a plurality of optical transmitters are arranged, preferably, uniformly distributed, along the periphery of said first device and that one optical receiver is arranged on said second device, with a switching unit being exclusively associated with said first device for selection of one of said transmitters.

3. Device according to claim 1, wherein at least one or a plurality of optical transmitters are arranged, preferably uniformly distributed along a first periphery of said first device and that two optical receivers are arranged on said second device, with a switching unit being exclusively associated with said second device for selection of one of said transmitters.

4. Device according to claim 1, 2, or 3, wherein at least one of the distances between a plurality of said optical transmitters or between a plurality of said optical receivers is equal to a multiple of the length of propagation of one bit of encoded data.

5. Device according to claim 1, 2, or 3, wherein at least one of the distances between a plurality of said optical transmitters or between a plurality of said optical receivers is equal to a multiple of the length of propagation of one data packet or frame of encoded data.

6. Device for transmitting optical signals between a first device and a second device, both devices being rotatable relative to each other, comprising:
at least one optical attached to said first device for emission of optical signals;
at least one optical receiver attached to said second device for receiving said optical signals;
at least one optical medium, preferably a light guide for transferring or guiding said optical signals;
said optical transmitters or receivers being arranged so that at any time at least one of said optical transmitters is connected via one of said optical media to at least one of said optical receivers; and
wherein the total of the numbers of optical transmitters and optical receivers amounts to at least three and that the sense of rotation between said first device and said second device is inverse to the sense of the direction of propagation of said optical signals, and that at least one switching unit is provided that selects optionally one of a plurality of optical transmitters or one of a plurality of optical receivers in such a way that precisely one optical transmitter, and one optical receivers is activated at one time for transmission between said first device and said second device, and that means are provided in said first device for repeating the emission of data.

7. Device according to claim 6, wherein a first set of controllable delaying elements is assigned to said optical transmitters or a second set of controllable delaying elements is assigned to said optical receivers.

8. Method of wide-band signal transmission between units being arranged rotably relative to each other, comprising:
generation of a serial data stream;
generation of optical signals in correspondence with the serial data emitting of said optical signals in the direction of movement switching over between various optical transmitters or receivers, so that the directions of emission will be retained even after the passage of transmitters and receivers; and
cancelling of multiply transmitted data.

* * * * *

UNITED STATES PATENT AND TRADEMARK OFFICE
CERTIFICATE OF CORRECTION

PATENT NO. : 6,937,787 B2
DATED : August 30, 2005
INVENTOR(S) : Schilling et al.

It is certified that error appears in the above-identified patent and that said Letters Patent is hereby corrected as shown below:

<u>Column 9,</u>
Line 39, after "Device for" delete "the" and after "transmitter", delete "of".

<u>Column 10,</u>
Line 26, after "at lease one optical" insert -- transmitter --.
Line 45, after "and one optical" delete "receivers" and substitute -- receiver --.

Signed and Sealed this

Sixth Day of June, 2006

JON W. DUDAS
*Director of the United States Patent and Trademark Office*